US006399622B1

(12) United States Patent
Lerner

(10) Patent No.: US 6,399,622 B1
(45) Date of Patent: Jun. 4, 2002

(54) METHOD FOR DIAGNOSING AND ALLEVIATING THE SYMPTOMS OF CHRONIC FATIGUE SYNDROME

(76) Inventor: A. Martin Lerner, 525 Harmon, Birmingham, MI (US) 48009

( * ) Notice: Subject to any disclaimer, the term of this patent is extended or adjusted under 35 U.S.C. 154(b) by 0 days.

(21) Appl. No.: 09/971,291

(22) Filed: Oct. 3, 2001

Related U.S. Application Data

(63) Continuation-in-part of application No. 09/663,729, filed on Sep. 15, 2000, which is a continuation-in-part of application No. 09/177,942, filed on Oct. 23, 1998, now Pat. No. 6,258,818, which is a continuation-in-part of application No. 08/802,776, filed on Feb. 18, 1997, now Pat. No. 5,872,123.

(51) Int. Cl.$^7$ .................. A61K 31/505; A61K 31/70

(52) U.S. Cl. .................. 514/258; 514/259; 514/260; 514/49

(58) Field of Search .................. 514/258, 259, 514/260, 49

(56) References Cited

U.S. PATENT DOCUMENTS

| | | | |
|---|---|---|---|
| 4,544,634 A | 10/1985 | Krenitsky | 435/119 |
| 4,695,570 A | 9/1987 | Krenitsky | 514/261 |
| 4,897,394 A | 1/1990 | Zimmerman et al. | 514/258 |
| 4,957,924 A | 9/1990 | Beauchamp | 514/262 |
| 5,055,296 A | 10/1991 | Wagle et al. | 424/553 |
| 5,061,708 A | 10/1991 | Krenitsky | 514/262 |
| 5,079,252 A | 1/1992 | Beauchamp | 514/262 |
| 5,189,022 A | 2/1993 | Bridge et al. | 514/16 |
| 5,206,008 A | 4/1993 | Loria | 424/45 |
| 5,213,106 A | 5/1993 | Lerner | 128/696 |
| 5,267,570 A | 12/1993 | Preston | 128/731 |
| 5,312,817 A | 5/1994 | Snorrason | 514/141 |
| 5,357,968 A | 10/1994 | Lerner | 128/696 |
| 5,405,850 A | 4/1995 | Blumenkopf | 514/262 |
| 5,426,028 A | 6/1995 | Levy et al. | 435/7.24 |
| 5,461,042 A | 10/1995 | Loria | 514/182 |
| 5,464,020 A | 11/1995 | Lerner | 128/696 |
| 5,491,150 A | 2/1996 | Aoki et al. | 514/310 |
| 5,538,856 A | 7/1996 | Levy et al. | 435/7.24 |
| 5,545,550 A | 8/1996 | Grossberg et al. | 435/240.2 |
| 5,545,670 A | 8/1996 | Bissbort et al. | 514/562 |
| 5,872,123 A | 2/1999 | Lerner | 514/258 |
| 6,258,818 B1 | 7/2001 | Lerner | 514/258 |

OTHER PUBLICATIONS

"A New Cardiomyopathy: A Pilot Study of Intravenous Ganciclovir in a Subset of the Chronic Fatigue Syndrome", A. Martin Lerner, et al. Depts. of Medicine, Wm. Beaumont Hospital, Wayne State Univ., Sch. of Med., Royal Oak, MI 1997 6:110–117.

"Perspectives on Interactions of Acyclovir with Epstein–Barr and Other Herpes Virus" Joseph S. Pagano, M.D., and Alok K. Datta, Ph.D. *Acyclovir Symposium–The American Journal of Medicine* 1982; 73; pp. 18–26.

"Valacyclovir HC1 (Valtrex) Provides Simplified Dosing and Increased Efficacy in the Treatment of Herpes Virus Infections" *Int. Pharm. Abstr.* 1994; 31:2244–5. Abstract No. 3111836.

"The Chronic Fatigue Syndrome: A Comprehensive Approach to Its Definition and Study", Keiji Fukuda, M.D., et al Annals of Internal Medicine, vol. 121, No. 12, pp. 953–959.

"Lack of Evidence for Infection with Known Human and Animal Retroviruses in Patients with Chronic Fatigue Syndrome", Clin. Infec. Disease 18, Suppl. 1, 1994, pp. S121–125.

"Long–Term Serological Follow–Up of Patients for Epstein– Barr Virus After Recovery from Infectious Mononucleosis", The Journal of Infectious Diseases, S. Horwitz, vol. 151, No. 6, Jun., 1985, pp. 1150–1153.

"Studies on Enterovirus in Patients with Chronic Fatigue Syndrome", J.W. Gow, et al Clinical Infectious Diseases, 1995; 18 (Suppl. 1), pp. S126–129.

"Molecular Biology and Immunology of Cytomegalovirus", Paul D. Griffiths and Jane E. Grundy, Biochem. J., (1987) vol. 241, pp. 313–324.

"Herpes Simplex Encephalitis–Vidarabine Therapy and Diagnostic Problems", Richard J. Whitley, et al; The New England Journal of Medicine, Feb. 5, 1981; vol. 304, No. 6, pp. 313–318.

"In Situ Detection of Human Cytomegalovirus Immediately–Early Gene Transcripts, etc." Tzyy–Choou Wu, et al, AIDS, 1992, vol. 6, No. 8, pp. 777–785.

"Cytomegalovirus as a Possible Cause of a Disease Resembling Infectious Mononucleosis" E. Klemola and L. Kaariainen, British Medical Journal, 1965, vol. 2, pp. 1099–1102.

"Infectious Mononucleosis", James C. Niederman, et al, Journal of The American Medical Association, 1968, vol. 203, No. 3, pp. 205–209.

"Medical Consequences of Persistent Viral Infection", Peter Southern and Michael B.A. Oldstone, New England Journal of Medicine, vol. 314, No. 6, pp. 359–367.

"Lack of Evidence for Infection with Known Human and Animal Retroviruses in Patients with Chronic Fatigue Syndrome", Walid Heneine, et al, Clinical Infectious Diseases 1994; 18 (Suppl. 1), pp. S121–S125.

(List continued on next page.)

Primary Examiner—Russell Travers
(74) Attorney, Agent, or Firm—Brooks & Kushman P.C.

(57) ABSTRACT

A method for alleviating chronic fatigue syndrome with the administration of antiviral agents. Based on clinical tests, chronic fatigue syndrome is a persistent herpes virus infection including incomplete virus multiplication and thus administration of antiviral agents are shown to alleviate the symptoms associated with the disorder. Based on therapeutic trials, patients receiving the recommended antiviral treatment, have experienced significant reduction or elimination of the symptoms associated with chronic fatigue syndrome. A method of diagnosis of the chronic fatigue syndrome is further disclosed.

2 Claims, 2 Drawing Sheets

OTHER PUBLICATIONS

"Repetitively Negative Changine T Waves at 24-h Electrocardiographic Monitors in Patients with the Chronic Fatigue Syndrome", A. Martin Lerner, et al; Chest vol. 104, No. 5, Nov. 1993, pp. 1417–1421.

"Abnormal Left Ventricular Myocardial Dynamics in Eleven Patients with Chronic Fatigue Syndrome", Clinical Nuclear Medicine, Aug. 1994, vol. 19, No. 8, pp. 675–677.

"Abnormal Left Ventricular Myocardial Dynamics in Patients with the Chronic Fatigue Syndrome in Birmingham, Michigan 1987–1994", A. Martin Lerner, et al, Wm. Beaumont Hospital, Royal Oak, MI; Wayne State Univ., Detroit, MI; Univ. of Michigan, Ann Arbor.

"Immune Surveillance Against Epstein–Barr Virus", Denis J. Moss, et al, Immunology, vol. 4, 1992, pp. 97–104.

"A Second Site for Epstein–Barr Virus Shedding: The Uterine Cervix", John W. Sixbey, et al, The Lancet, Nov. 1986, pp. 1122–1124.

"Prolonged Inhibitory Effect of 9–(1, 3–Dihydroxy–2–Propoxymethyl)Guanine Against Replication of Epstein–Barr Virus", Jung–Chung Lin, et al, Journal of Virology, Apr., 1984, vol. 50, No. 1, pp. 50–55.

"Epstein–Barr Virus Replication in Oropharyngeal Epithelial Cells", John W. Sixbey, et al, The New England Journal of Medicine, vol. 310, No. 19, 1984, pp. 1225–1230.

"Chronic Epstein–Barr Virus Infection Associated with Fever and Interstitial Pneumonitis", Robert T. Schooley, et al, Annals of Internal Medicine, 1986, vol. 104, pp. 636–643.

"Long–Term Serological Follow–Up of Patients for Epstein– Barr Virus After Recovery from Infectious Mononucleosis", Charles A. Horowitz, et al, The Journal of Infectious Diseases, vol. 151, No. 6, Jun. 1985, pp. 1150–1153.

"Is Neurally Mediated Hypotension an Unrecognised Cause of Chronic Fatigue?", Peter C. Rowe, et al, The Lancet, vol. 345, pp. 623–624.

"Chronic Fatigue Syndrome", Principles and Practice of Infectious Diseases–4th Ed., R. T. Schooley, 1995, pp. 1306–1310.

"Acyclovir Treatment of the Chronic Fatigue Syndrome", Stephen E. Straus, et al, The New England Journal of Medicine, vol. 319, No. 26, pp. 1692–1698.

"The Chronic Fatigue Syndrome—One Entity or Many?", Morton N. Swartz, The New England Journal of Medicine, vol. 319, No. 26, 1988, pp. 1726–1728.

"The Relationship Between Neurally Mediated Hypotension and the Chronic Fatigue Syndrome", Issam Bou–Holaigah, et al, Journal of The American Medical Association, vol. 274, No. 12, pp. 961–967.

"A Cluster of Patients with a Chronic Mononucleosis–like Syndrome: Is Epstein–Barr Virus the Cause?", G.P. Holmes, et al, Journal of The American Medical Association, 1987, vol. 257, No. 17, pp. 2297–2302.

"Frequency of 'Chronic Active Epstein–Barr Virus Infection' in a General Medical Practice", Dedra Buchwald, et al, Journal of The American Medical Association, 1987, vol. 257, No. 17, pp. 2303–2307.

"The Epstein–Barr Virus: Host Balance in Acute Infectious Mononucleosis Patients Receiving Acyclovir Anti–Viral Therapy", Q.Y. Yao, Int. J. Cancer, 1989, vol. 43, pp. 61–66.

"A Double–Blind, Placebo–Controlled Trial of Intravenous Immunoglobulin Therapy in Patients with Chronic Fatigue Syndrome", Andrew Lloyd, et al, The American Journal of Medicine, 1990, vol. 89, pp. 561–568.

"A Controlled Trial of Intravenous Immunoglobulin G in Chronic Fatigue Syndrome" P.K. Peterson, et al, The American Journal of Medicine, 1990, vol. 89, pp. 554–560.

"Chronic Fatigue Syndrome: A Working Case Definition", G.P. Holmes, et al Annals of Internal Medicine, 1988, vol. 108, pp. 387–389.

"Leukocyte–Transforming Agent: Prolonged Excretion by Patients with Mononucleosis and Excretion by Normal Individuals", H. Dean Golden, et al, The Journal of Infectious Diseases, 1973, vol. 127, No. 4, pp. 471–473.

"Enhanced Serological and Virological Findings of Epstein–Barr Virus in Patients with AIDS and AIDS–Related Complex", Ciro V. Sumaya, et al, The Journal of Infectious Diseases, 1986, vol. 154, No. 5, pp. 864–870.

"Human Herpes Virus–6: Clinical Implications of a Recently Discovered, Ubiquitous Agent", Charles T. Leach, The Journal of Pediatrics, 1992, vol. 121, No. 2, pp. 173–181.

"Summary: Viral Studies of Chronic Fatigue Syndrome", Dharam V. Ablashi, Clinical Infectious Diseases, 1994:18 (Suppl. 1), pp. S130–S133.

"Epstein–Barr Virus–Specific IgA Serum Antibodies as an Outstanding Feature of Nasopharyngeal Carcinoma", Gertrude Henle, et al, Int. J. Cancer, 1976, vol. 17, pp. 1–7.

"Viral Latency and Transformation: The Strategy of Epstein– Barr Virus", George Klein, Cell, 1989, vol. 58, pp. 5–8.

"IgM Antibodies Specific for Epstein–Barr Virus in Infectious Mononucleosis Without Heterophil Antibodies", J. Nikoskelainen, et al, British Medical Journal, 1974, vol. 4, pp. 72–75.

"Repression of Human Cytomegalovirus Major Immediate Early Gene Expression in a Monocytic Cell Line", J. H. Sinclair, et al, Journal of General Virology (1992) vol. 73, pp. 433–435.

"Chest Pain and Palpitation", Eugene Braunwald, Harrison's Principles of Internal Medicine (10th Ed.), (1983) pp. 25–31.

"Chronic Fatigue Syndrome–Information for Physicians", National Institute of Allergy and Infectious Diseases, National Institutes of Health, Sep., 1996 pp. 1–16.

"Acyclovir Treatment of the Chronic Fatigue Syndrome", Stephen Straus et al., 1988 New England Journal of Medicine, Dec. 29, 1988, vol. 319, No. 26, pp. 1692–1698.

"New Cardiomyopathy: Pilot Study of Intravenous Ganciclovir in a Subset of the Chronic Fatigue Syndrome", A. Martin Lerner et al., Departments of Medicine, Wm. Beaumont Hospital, Wayne State Univ., School of Medicine, 1997, 6:110–117.

"A Preliminary 6 Month Trial of Valacyclovir (VAL) in Chronic Fatigue Syndrome (CFS) Using the Epstein–Barr Virus (EBV), Cytomegalovirus (HCMV) Paradigm", A. Martin Lerner et al., Abstract for $36^{th}$ Annual Meeting of the Infectious Disease Society of America.

"*The Human Herpesviruses*", edited by B. Roizman, R.J. Whitley & C. Lopez, Raven Press Ltd., New York, 1993, Chapters 4, 5, 6 and 11.

"A Preliminary Randomized Double–Blinded Controlled Six Month Trial of Valacyclovir in Chronic Fatigue Syndrome Using the Epstein–Barr Virus/Cytomegalovirus Paradigm," A. Martin Lerner, et al., 36TH Annual Meeting of the Infectious Diseases Society of America, Nov. 23–15, 1998, Denver, CO.

"Stress/Rest Radionuclide Cardiac Ventriculography in Chronic Fatigue Syndrome," A. Martin Lerner, et al., presented in part at the 35th Annual Meeting of the Infectious Diseases Society of America, Sep. 15, 1997, San Francisco, CA.

Lerner, A. Martin; Zervos, Marcus; Chang, C.H.; Beqaj, Savedin; Goldstein, James; O'Neill, William; Dworkin, Howard; Fitzgerald, Thomas; and Deeter, Robert G.; A Small Randomized Placebo–Controlled Trial of the use of Antiviral Therapy for Patients with Chronic Fatigue Syndrome, *Clinical Infectious Diseases* 2001, vol. 32, pp. 1657–1658.

Valcyte™ (valganciclovir hydrochloride tablets), pamphlet published and distributed by Roche Pharmaceuticals, Roche Laboratories, Inc., Nutley, NJ 07110, issued Mar. 2001.

Brown, Frances; Banken, Ludger; Saywell, Kay; and Arum, Inger; Pharmacokinetics of Valganciclovir and Ganciclovir Following Multiple Oral Dosages of Valganciclovir in HIV– and CMV–Seropositive Volunteers, Adis International Limited; Clin Pharmacokinet Aug. 1999: 37 (2), 167–176.

Jung, Donald, Ph.D.; and Dorr, Albert, Ph.D.; Single–Dose Pharmacokinetics and Valganciclovir in HIV– and CMV–Seropositive Subjects, Pharmacokinetics and Pharmacodynamics, J. Clin Pharmacol 1999; 39:800–804.

METHOD FOR DIAGNOSING AND ALLEVIATING THE SYMPTOMS OF CHRONIC FATIGUE SYNDROME

CROSS-REFERENCE TO RELATED APPLICATIONS

This application is a continuation-in-part of U.S. application Ser. No. 09/663,729 filed Sep. 15, 2000, which is a continuation-in-part of U.S. application Ser. No. 09/177,942 filed Oct. 23, 1998, now U.S. Pat. No. 6,258,818 which, in turn, is a continuation-in-part of prior U.S. application Ser. No. 08/802,776 filed Feb. 18, 1997, now U.S. Pat. No. 5,872,123.

TECHNICAL FIELD

This invention relates to a method of alleviating the symptoms associated with chronic fatigue syndrome through the use of antiviral agents.

BACKGROUND ART

Chronic fatigue syndrome (CFS) is a disorder which, until recently, had no formalized name, received little attention and was believed by the majority of the medical community to be a psychological rather than medical disorder. However, as information about the disorder has been disseminated, the symptoms associated with the disorder, as well as the growing number of people afflicted with this disorder, have steadily increased to alarming proportions. In fact, CFS is being reported with increasing frequency throughout the world.

Chronic fatigue syndrome is a puzzling, exasperating illness whereby previously healthy, vigorous and productive young or middle-aged adults are suddenly afflicted with a persistent, overwhelming fatigue. When such a severe debilitating fatigue extends beyond six months and psychiatric disease is excluded, the condition has been termed "chronic fatigue syndrome." Despite the number of people afflicted with chronic fatigue syndrome and the recent research attention, to date, the cause of the disorder remains unknown.

The medical community has only recently defined the term "chronic fatigue syndrome" to have a distinct and well-defined meaning. In the *Journal of the Royal Society of Medicine*, Vol. 84, February, 1991, chronic fatigue syndrome is defined as:

"A fatigue which is the principal symptom, which has a definite onset, and is severe, disabling and affects both physical and mental functioning, and furthermore that fatigue should have been present for a minimum of six months at which it was present for more than 50% of the time."

One or more of the following symptoms are generally associated with the syndrome, such as sleep disturbances (changes in the duration of sleep and/or quality of sleep), impairments in concentration and short-term memory, chronic and recurrent low-grade fever, and musculoskeletal pain. The changes in the duration of sleep could be hypersomnia or increased sleep, or insomnia or reduced sleep. The changes of the quality of sleep are contemplated to be due to a decrease of REM sleep. There is also generally a restriction or lack of ability to perform an activity in the manner or within the range considered normal for a healthy human being, (resulting from loss of psychological or physiological function). There is further a definite persistent change from a previous level of functioning.

Mood disturbances such as depressed mood, and anhedonia, anxious mood, emotional stability, irritability, and severity of the mood disturbances should be assessed on standards scales. For diagnosis purposes, a patient's symptoms should be evaluated to determine whether such symptoms are attributed by a psychological condition, such as a depressive disorder rather than chronic fatigue syndrome. It should thus be determined whether the disorder is sufficient to meet the diagnostic criteria for major depressive disorders. In CFS patients, myalgia, which is pain or aching felt in the muscles, should be disproportionate to exertion. Such myalgia should be distinguished from feelings of weakness and pain felt in other areas such as the joints. Certain patients should be excluded from the definition of CFS, such as patients with established medical conditions known to produce chronic fatigue such as severe anemia. Additionally, patients with schizophrenia, manic depressive illness, substance abuse, eating disorders, or proven organic brain disease should be excluded as chronic fatigue syndrome sufferers. However, other generalized psychiatric disorders may be attributed to chronic fatigue syndrome.

A variety of treatments have been suggested and utilized for the treatment of chronic fatigue syndrome. In U.S. Pat. No. 5,312,817, there is described a treatment of the chronic fatigue syndrome wherein a pharmaceutically-acceptable cholinesterase inhibitor or a prodrug therefore is administered for the treatment of fatigue syndromes. This treatment is based on the understanding that the mechanism of the fatigue could be an imbalance in the cholinergic nicotinic transmitter system, both peripherally and centrally, which decreases the acetylcholine in the central and peripheral synapses. However, this therapy has proven ineffective, as this mechanism does not properly describe the etiology of chronic fatigue syndrome.

In a further example, U.S. Pat. No. 5,055,296 discloses a treatment involving the administration of mammalian liver extract. Yet another example is provided in U.S. Pat. No. 5,013,739, whereby an opiate receptor antagonist is administered as a treatment option. In addition, a variety of drugs have been prescribed for symptomatic relief including non-steroidal anti-inflammatory drugs, tricyclic anti-depressants, sleep-inducing drugs, tranquilizers, anti-anxiety and stress-relieving drugs such as androstenediol and androstenetriol. Such symptomatic treatment efforts, while providing temporary relief for one of the associated symptoms, have in general provided no long-term treatment of the disorder as a whole.

In addition to the physical pain associated with this disorder, there is also a severe mental and emotional toll placed on the CFS sufferer. As a result of the prolonged and debilitating fatigue, and flu-like symptoms, CFS sufferers are forced to reduce their level of activity, and are often unable to lead what would be considered a normal life.

Accordingly, there is a genuine need for a method of treating chronic fatigue syndrome with a reliable, and effective technique which allows a CFS sufferer to regain a normal level of activity without the associated persistent fatigue characterized by the disorder.

DISCLOSURE OF INVENTION

It would be desirable to provide a method for alleviating the symptoms associated with chronic fatigue syndrome by administering antiviral agents to target the cause of the disorder. It would further be desirable to provide a treatment for chronic fatigue syndrome through administration of an antiviral drug which is directed to the cause of chronic fatigue syndrome rather than one that addresses a particular condition or symptom. It would be yet further desirable to provide a long-term treatment approach whereby chronic fatigue sufferers could resume a normal level of activity without experiencing extreme fatigue.

In carrying out the above objects, a method is disclosed for alleviating the symptoms of chronic fatigue syndrome, including administering to a patient in need there of, a therapeutically effective amount of one or more pharmaceutically acceptable antiviral agents, wherein the one or more antiviral agents are selected from the group consisting of acyclovir, ganciclovir, valacyclovir, famciclovir, cidofovir, and pharmaceutically acceptable derivatives and mixtures thereof.

There is further disclosed a method of diagnosing chronic fatigue syndrome (CFS) in a patient, including the steps of: evaluating the patient for serologic evidence of Epstein-Barr virus (EBV) and human cytomegalovirus (HCMV) infection; and monitoring the patient for T-wave abnormalities by 24-hour electrocardiographic (Holter) monitoring to document the persistent cardiac pathology which is the basis of the CFS. The serologic evidence of EBV and HCMV is obtained by studying the level of antibodies of EBV and HCMV to detect the presence of active and persistent multiplication of either or both of the viruses. In conjunction therewith, tests are conducted to verify the existence of a cardiomyopathy in the CFS patient. Based on the results of the tests and the determination of the cause of CFS, the patient is administered a specific antiviral agent suitable for EBV, HCMV or the combination. Following initial antiviral treatment, supplemental tests are conducted to check for recurrent CFS to determine an appropriate treatment period for the patient to achieve continued alleviation of the CFS symptoms.

There is yet another method of diagnosing CFS in a patient including the steps of: evaluating the patient for serologic evidence by HCMV, evaluating assays for non-structural early gene products; and monitoring the patient for T-wave abnormalities by 24-hour Holter monitoring to document the persistent cardiac pathology which is the basis of the CFS.

The above objects and other objects, features, and advantages of the present invention are readily apparent from the following detailed description of the best mode for carrying out the invention.

BRIEF DESCRIPTION OF DRAWINGS

FIG. 1b is an illustration of the herpes virus genome partially opened;

FIG. 1c is an illustration of the herpes virus genome opened, in its linear position;

BEST MODE FOR CARRYING OUT THE INVENTION

Figure 1A:
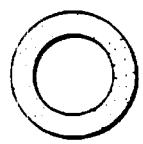
FIG. 1a is an illustration of a latent herpes virus genome sitting as a closed nuclear episome.

As defined herein, a "therapeutically effective" amount of an antiviral agent is the amount by which a patient's chronic fatigue syndrome symptoms, such as severe fatigue, headaches, sore throats and the like, decrease in frequency and/or intensity. In addition, the term "alleviating" as used throughout th e specification refers to relieving or reducing symptoms associated with chronic fatigue syndrome and/or elimination of those symptoms.

Likewise, the term "pharmaceutically acceptable antiviral agent" is defined to include those antiviral agents which, upon administration, have no deleterious effect on the patient. Thus, where a particular antiviral agent is unsuitable for a particular individual, that antiviral agent would not be pharmaceutically acceptable and would thus not be administered.

In general, the clinical symptoms and signs of chronic fatigue syndrome resemble those of infectious mononucleosis. Symptoms common to both illnesses include low-grade fevers, chills, sore throats, painful anterior or posterior cervical or axillary lymph nodes, muscle weakness, myalgias, generalized headaches, migratory arthralgias, vague neuropsychological complaints and disturbances of sleep without known medical cause. As with mononucleosis, a CFS patient's attempt to exercise at levels previously tolerable, results in a prolonged and more severe manifestation of the fatigue.

While CFS and infectious mononucleosis have several similarities, patients with CFS do not have the severe dysphagia and gray exudative pharyngitis often accompanied by submandibular adenopathy, associated with infectious mononucleosis and its etiologic agent Epstein-Barr virus (EBV). Our research has found in CFS sufferers the existence of Epstein-Barr virus multiplication, purportedly within epithelial cells of the pharynx and circulating B-lymphocytes of the blood. The beta herpes virus, human cytomegalovirus (HCMV) is also believed to cause infectious mononucleosis-type symptoms, without the exudative pharyngitis. Mononucleosis and chronic fatigue syndrome thus have certain similar symptoms.

Specific emphasis must however be placed on symptoms unique to chronic fatigue syndrome. Such symptoms include: 1) light-headedness or wooziness of varying severity and duration without known antecedent cause; 2) a vague, dull, pressure-like chest ache, generally in the substernal region and sometimes including the left shoulder, which is exhibited with increasing fatigue at the end of the day; and 3) palpitations. There is also often a fourth symptom, tachycardia or rapid heart action, even with minimal or no exertion by the sufferer. Based on the symptoms unique to chronic fatigue syndrome, it is further hypothesized, that chronic fatigue syndrome is essentially cardiac in origin, and that this cardiac basis unlocks the key to the disorder.

Accordingly, while not wishing to be bound to any particular theory, it is believed that the majority of cases of chronic fatigue syndrome constitute either a continuing primary herpes virus infection, specifically Epstein-Barr virus and/or human cytomegalovirus, or alternatively, a reactivation infection with latent Epstein-Barr virus and/or latent human cytomegalovirus. In some lesser number of cases, herpes virus 6 (HHV-6), or other viruses, such as enteroviruses may be involved. Seroepidemiologic studies indicated the presence of EBV and/or HCMV in CFS sufferers. Our research has further indicated for CFS sufferers the existence of IgM antibodies to the EBV viral capsid antigen (VCA) or EBV antibodies to diffuse early antigen (EA), the latter depicting EBV transactivators for the lytic cycle indicating current virus multiplication. In CFS sufferers, there may additionally or alternatively be a significant IgG immunoreactive antibody (ELISA) to HCMV, with/without an IgM (ELISA) antibody titer to HCMV.

The understood virologic cause of CFS thus verifies that previous seroepidemiologic studies attempting to show a singular virologic causation to CFS including singular searches for EBV or HCMV antibodies would have naturally yielded uniformly negative results. At least fifteen different viruses, bacteria and parasites have been previously suspected as "singular" etiologic agents of CFS. However, there has been, to date, no serologic association with any human virus. It is believed that the previous studies were designed in a way that actually masked the possibility of finding a major two-virus causality.

Instead, the extra-chromosomal herpes virus episome persists for the life of th e chronically infected cell. The persistent infection and recrudescent infection characteristic of the herpes virus is common in EBV and HCMV and is consistent with the chronic recrudescent illness of CFS. The unique aspect of this cellular injury, particularly in the heart, is that it appears to be a degenerative disease which does not elicit an inflammatory response from the host. The result is a cardiomyopathy of unknown cause.

The two proposed major causative herpes viruses, EBV and HCMV, are characterized by persistent infections. In a non-permissive, persistent infection, a complete infectious virus is not produced. This is referred to as incomplete herpes virus multiplication. Intracellular infection produces a metabolically altered host cell, however, no progeny capable of infecting a new susceptible cell are created. The host human is unsuccessful in totally inactivating the virus and placing it in the latent state. The virus likewise is unsuccessful in completing its reproductive cycle and produces incomplete virus. The result is cellular metabolic aberration and, if severe enough, cell death—called apoptosis.

The herpes virus is described as three states of infection: 1) virulent; 2) latent; and 3) incomplete virus multiplication. It is also theoretically possible at the same time to have both infections with a portion of it being virulent and a portion of it being incomplete virus multiplication.

Figure 1D:
FIG. 1d is an illustration of the complete herpes viral structure.
Figure 1D:
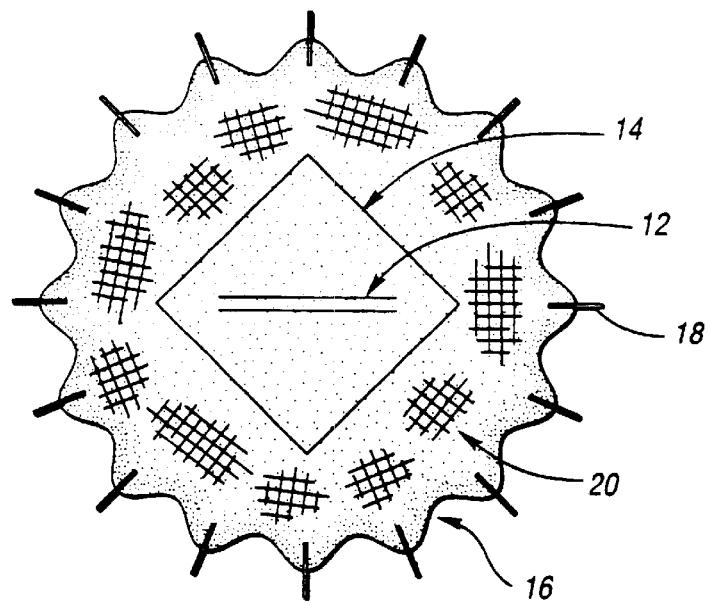

FIG. 1 is a depiction showing latent herpes virus genome. The herpes viruses in question are hu man cytomegalovirus and human Epstein-Barr virus which are believed to cause chronic fatigue syndrome. In the most optimum circumstance after infection with either of the two aforementioned herpes viruses, t he virus sits as a closed nuclear episome as shown in FIG. 1a in a non-integrated fashion with the cellular genome. The herpes virus is double-stranded. It is complete and it is theoretically making no gene product, FIG. 1a.

The herpes virus genome is capable of making over 200 gene products and 200 separate proteins. In FIG. 1c the latent double-stranded DNA has opened—is in its linear position and ready to produce its gene products and the proteins of the complete virus. In FIG. 1b, the herpes virus genome is partially opened from its cellular state and is able to produce some proteins of the virus. Some of the gene products are produced but no complete virus is developed. This then is incomplete virus replication. In FIG. 1d, we see the complete viral structure 10. It consists of a central double-stranded complete virus DNA 12 surrounded by an icosahedral capsid containing 162 identical, symmetrical, capsomers. The outer portion of the complete virion is a double-layered lipid membrane 16 which is punctuated by glycoprotein spikes 18. These glycoprotein spikes 18 are the means of attachment of this herpes virus to susceptible cells allowing entry and new infection of a previously uninfected cell. The human response, the immune system, responds to the antigenic stimulus of the structural proteins available to the human host by these glycoprotein spikes 18.

Between the herpes virus bilayer 16 and the viral capsid 14 is an amorphous structure known as the tegument 20. This tegument 20 contains nonstructural proteins which are necessary for multiplication of the virus. It contains a number of viral enzymes and factors necessary for viral assembly. A complete herpes virus virion 10 is depicted in FIG. 1d. Antibodies to structural glycoprotein, for instance gB and gH of human cytomegalovirus, are produced. In the case of incomplete virus replication, the herpes virus genome is partially opened and producing some proteins. These aberrant proteins are not wanted in the healthy cellular matrix and efforts to rid the matrix of these partial viral gene products is made by the process of exocytosis. By this process of exocytosis, nonstructural gene products (e.g. UL44 and UL57) reach the extracellular space and are thus available to the human host immune system so that specific antibodies may be produced to these nonstructural gene products, UL44 and UL57. These nonstructural gene products are behind the virus bilayer 16 and are not exposed to antibody production when whole complete virus multiplication occurs.

There is evidence that supports the theory that both HCMV and EBV are cardiotropic for the human myocyte. Based on our research, it is believed that the human cardiac myofiber, like the B-lymphocyte for EBV and the mononuclear progenitor cell for HCMV, is a site of non-infectious episome-mediated persistent infection. This is different from the human epithelial cell of the pharynx which produces mainly whole infectious EBV virus. HCMV immediate-early gene transcripts have been detected in the heart by in-situ hybridization techniques in patients with HIV-associated cardiomyopathy. Likewise, the EBV genome was detected by polymerase chain reaction amplification of DNA extracted from the heart at autopsy. An intense mononuclear cell infiltrate in the myocardium consisted essentially of T-cells without identifiable B-cells. This inflammatory response is the result of complete virus multiplication.

Accordingly, our research has indicated that CFS is a non-permissive, persistent herpes virus infection of the heart, wherein EBV and/or HCMV nucleic acids are present in the hearts of CFS patients. This hypothesis was generated based in part upon endomyocardial biopsies of patients with CFS. HCMV nucleic acids by polymerase chain reaction have been found in biopsies of the heart from CFS patients.

The research conducted revealed that all CFS patients have abnormal oscillating T-wave flattenings and T-wave inversions detectable from 24-hour electrocardiographic (Holter) monitoring. An initial 24-hour electrocardiographic T-wave study compared CFS patients to random non-CFS patients, from an internal medicine practice, wherein both patient groups were restricted to an age less than 50 years old to minimize the occurrence of chronic diseases in both populations. Notably, chronic diseases such as hypertensive vascular disease, electrolyte abnormalities and coronary artery disease may produce similar oscillating abnormal T-waves. However, since people suffering from CFS are generally young, such chronic diseases rarely afflict CFS sufferers and can thus be excluded as the causative agent. Oscillating T-wave abnormalities described also occur in about 5% of normal patients when they assume an upright position. For these same patients, resting twelve-lead standard ECG, T-waves describing left ventricular electrical depolarization are upright, and the resultant ECG is normal. The 2-D echocardiogram also generally is normal, however, the 24-Hr. ECG recordings (Holter monitoring) are abnormal with oscillating T-wave flattenings or T-wave inversions characteristically incident with the onset of sinus tachycardias, and subsequently, reverting to normal T-wave configurations with the return of normal sinus rhythms. While these abnormal T-waves are not specific to CFS, they occur similarly with diverse conditions such as coronary artery disease, hypertensive vascular disease and electrolyte abnormalities, but the abnormal T-waves detected via Holter monitoring were seen much more frequently in 24 random CFS patients than 116 time, place and age-matched random non-CFS patients. Based on our analysis, the abnormal T-waves at 24-Hr. ECG recordings in CFS patients are not "artifacts," and are a significant sign of CFS. The abnormal Holter monitoring in CFS patients is evidence that CFS is a cardiomyopathy. Moreover, we have found that the additional symptoms of a dull chest ache coming on at the end of the day not related to exercise, light-headedness or wooziness and palpitations are CFS symptoms attributable to cardiac involvement by these viruses.

Holter monitoring is further utilized and discussed in more detail in U.S. Pat. No. 5,454,020 issued to A. Lerner on Nov. 7, 1995; U.S. Pat. No. 5,357,968 issued to A. Lerner on Oct. 25, 1995; and U.S. Pat. No. 5,213,106 issued to A. Lerner on May 25, 1993.

An initial group of CFS patients, additionally, demonstrated abnormal left ventricular dynamics characterized by a decreased or falling ejection fraction, abnormal wall motion or dilatation by radionuclide stress multiple gaited acquisition (MUGA) studies. Furthermore, consecutive case series of CFS patients from a single referral center at Birmingham, Mich. during the years 1987–1993 demonstrated abnormal left ventricular dynamic function in 24.1% of 87 patients undergoing radionuclide ventriculography by the radioisotopic gaited pool method.

In an effort to diagnose CFS, using electron microscopy, cardiomyopathic changes including myofiber hypertrophy, myofiber disarray and degenerative change in myofibers have been seen. On rare occasions, inflammatory myocarditis is evident. Infectious HCMV is not found in the heart, peripheral blood or urine of this HCMV-CFS subset of patients. Based on the evidence gathered, it is believed conclusively that CFS is a major newly discovered cardiomyopathy.

On the basis of this research, chronic fatigue syndrome is understood further to be a persistent, non-permissive herpes virus infection of the heart. CFS patients have abnormal Holter monitoring reflecting that cardiomyopathy. Additionally, the majority of CFS patients have the appropriate serologic markers of persistent EBV and/or HCMV infections. Research has led to the understanding that HCMV and/or EBV nucleic acids are present in myofibers (myocytes) of cardiac tissues of the CFS patients which are detectible by polymerase chain reaction (PCR) or in-situ hybridization techniques. Additionally, it is believed that EBV and/or HCMV nucleic acids will not be present in the myofibers of EBV or HCMV serologically positive, non-CFS patients undergoing similar cardiac biopsies. We have further observed that patients with acute primary EBV infectious mononucleosis who recover rapidly have normal Holter monitoring throughout their illnesses. It is thus believed that these EBV-infected patients have no cardiomyopathies. On the contrary, patients with prolonged illnesses of acute primary EBV-infectious mononucleosis exhibit abnormal Holter monitoring which substantiates our understanding of the mechanism of CFS.

Given the pathologic physiology of herpes virus infections in humans, the etiologic diagnosis resulting from this research is not contradictory. Just like CFS, herpes simplex virus encephalitis (HSVE) boggled the medical community and etiologic identification due to the rising antibodies in serum which may or may not be present at a given time. Diagnosis of HSVE required isolation of herpes simplex virus, Type 1 from the brains of patients with encephalitis.

Rowe, Bou-Halaigah, Kan and Calkins recently reported that CFS patients exhibited an abnormal blood pressure response in an upright tilt position. The Relationship Between Neurally Mediated Hypotension and the Chronic Fatigue Syndrome, JAMA, 1995; 274: 961–967. This abnormal response was explained to be the result of an abnormal neural reflex caused by CFS. Our research disproves this theory, rather CFS is a cardiomyopathy inducing the reported abnormal cardiac response, which is further supported by the abnormal T-wave findings at Holter monitoring we have discovered.

Having tracked the etiologic agents of CFS, an intense study of EBV and HCMV followed. Epstein-Barr virus infection starts in the oropharyngeal epithelium. The cells in this region are permissive for virus replication and thus a persistent active lytic infection continues in this region for many years. It is believed that in the primary infection level, Epstein-Barr virus infects B lymphocytes. Similarly, the cellular sites for latency for HCMV are the mononuclear phagocyte and its progenitor cells. In the case of HCMV, when the monocyte differentiates into the macrophage or histiocyte, infectious HCMV virus production ensues with an associated irreversible destruction of the infected cell.

Epstein-Barr virus is the prototype for the lymphocryptovirus genus. The lymphocryptovirus is a closely related member of the gamma herpes virus family. The host range of these viruses in-vitro is restricted to primary lymphocytes of the immunoglobulin-producing lineage (B-lymphocytes). The lymphocytes are also a site of latent virus infection in-vivo. In-vivo, most human EBV infection starts in the oropharyngeal epithelium. Epithelium cells allow herpes virus replication and thus a persistent, active lytic infection continues for many years. During the course of primary infection, EBV infects B lymphocytes. EBV does not usually replicate in B lymphocytes but instead establishes latent infection. Early in human infection, EBV-infected B lymphocytes can be found in large numbers in peripheral blood and tissues.

Much evidence supports the understanding that lymphocytes or similar cell type are the major site of latent infection for EBV and are important in the dissemination of infection to distal epithelial surfaces or in continuously reactivating the oropharyngeal epithelium. The EBV infection generally follows a specific pattern of events. In a first instance, the virus initiates infection of the oropharyngeal epithelium, where it can produce symptomatic pharyngitis. B-lymphocytes are then infected as they reside in close proximity to the oropharyngeal epithelium. The lymphocytes then carry the virus to other organs and to epithelial surfaces, including the oropharynx. Furthermore, persistent replication in the oropharynx is likely dependent on lymphocyte reinfection of oropharyngeal epithelial cells. After the primary EBV infection, the emergence of Burkitt's lymphoma, Hodgkin's disease, and nasopharyngeal carcinoma is believed to be linked to EBV.

Most human peripheral blood B lymphocytes are susceptible to EBV infection. The cells become latently infected and are driven to proliferate by the latent virus genome.

People infected with EBV have B lymphocytes in the peripheral blood which are able to proliferate into long-term lymphoblastoid cell lines in vitro. All cell lines that grow out of the peripheral blood of normal humans are EBV-infected B lymphocytes. Thus, EBV provides B cells with the ability to multiply indefinitely.

The persistence of EBV in human populations appears to be dependent on oropharyngeal multiplication of virus, and salivary spread to the oropharynx of uninfected humans. Most disease manifestations are related to lytic infection in oropharyngeal epithelial cells, to latent virus infection in tonsillar or peripheral blood B lymphocytes or to immune responses to virus-infected cells.

Human cytomegalovirus (HCMV) like all of the herpes viruses, has in common certain distinguishing features, including virion and genome structure and the ability to establish persistent and latent infections. In addition to these common herpes virus features, HCMV has certain distinct characteristics, such as salivary gland tropism, species specificity and slow growth in cultured cells. HCMV infects 50% to 80% of the population. HCMV can be structurally distinguished from other herpes viruses by subtle ultrastructural differences in the virion appearance, for example, the HCMV envelope generally appears more pleomorphic in relation to other herpes viruses. HCMV generally produces cell enlargement with intranuclear inclusions similar to those produced by herpes simplex and varicella zoster virus. The sources of HCMV include oropharyngeal secretions, urine, cervical and vaginal excretions, spermatic fluids, breast milk, feces and blood.

With HCMV, a large reservoir of latently infected individuals remains a significant threat to the immunocompromised host. The virus persists years after the primary infection. However, the virus is detectible only for a few weeks to a few months following primary infection. The polymorphonuclear leukocyte is the main source of HCMV in the blood, but monocytes and occasionally T lymphocytes may harbor HCMV in a form as yet unknown.

Table 1 describes the antibody response to whole virus infection which results in antibodies to viral structural epitopes and a response to nonstructural viral epitopes such as would be seen in incomplete viral replication. Two common viral epitopes that are structural are human cytomegalovirus HCMV gB and HCMV gH. These are antigenic epitopes which are structural. These structural epitopes can be recognized by ELISA (enzyme linked immunoassay) or what is referred to as the Copalis® Multiplex light scatter method ("Copalis® method"). Copalis® (coupled particle light scattering) is the proprietary technology of Diasorin, Inc.

This Copalis® method to $CM_2$ and p52 measures IgM antibodies to HCMV non-structural gene products. The non-structural gene products are UL44, UL57. These gene products have been produced in *E-coli*. The UL44 and UL57 refer to the open reading frames (ORF) of the human cytomegalovirus genome. The UL44 has the function of a polymerase processivity factor known as p52. The UL57 is the second gene product which may be measured by the Copalis® method and its function is as a single-stranded (ss) DNA binding protein $CM_2$. These are nonstructural gene products which are extruded from a cell with incomplete human cytomegalovirus multiplication. The Copalis® method measures antibodies to these two gene products with the purified antigens produced in *E-coli*. Table 1 shows the types of herpes virus infection with antibody responses to both structural and nonstructural viral epitopes.

TABLE 1

HERPES VIRUS INFECTION

| Stage of Infection | Structural Viral Epitopes (e.g. HCMVgB, HCMVgH) | | Non-Structural Viral Epitope (e.g. HCMV) |
|---|---|---|---|
| | IgM | IgG | IgM, $CM_2$, p52 |
| Virulent (Complete) | X | X | |
| Latent | | X | |
| Incomplete | | X | X |
| Mixed | X | X | X |

In virulent virus infection, the infected cell is destroyed. Cellular inflammation in the classical sense results. Specific antibodies to structural epitopes of human cytomegalovirus for instance gB and gH result. This results in IgM and IgG antibodies. The IgM antibody, of course, is short-lived usually less than six weeks, and the IgG antibody is long-lived. In classical virulent infection no antibodies would be produced to nonstructural viral epitopes, hereinafter referred to as p52 (to UL44 and UL57) and $CM_2$ (UL57). In latent infection there is no complete virus produced. There is no IgM to structural epitopes gB and gH antibody. IgG antibody, of course, is present because there is past infection and, of course, there is no antibody to p52 or $CM_2$. In incomplete viral multiplication, no IgM antibodies to structural epitopes are produced. Of course, IgG antibodies are stable and present. In incomplete viral multiplication, IgM antibodies are produced to nonstructural epitopes (Table 1). Finally in mixed virulent and incomplete (or complete and incomplete viral replication/multiplication), one may have IgM antibodies and IgG antibodies to structural epitopes and IgM antibodies to nonstructural epitopes.

The Copalis® CMV Mutliplex assay is a homogenous test for the simultaneous determination of acute infection stages or immune status to Cytomegalovirus using coupled particle light scattering. Sized microparticles, coated with one of three antigens (p52, $CM_2$, and CMV viral particle (VP)) are dried in the reaction cup. Early phase IgM antibodies are detected by both the $CM_2$ and the p52 antigens. Antibody response to the $CM_2$ antigen but not to the p52 antigen continues through the convalescent stage of acute infection. Antibodies to the VP may appear during acute infection but shall persist during life. Reactivity just (sucrose-density purified tissue culture produced complete HCMV cytomegalovirus) to the VP is characteristic of prior infection (indicative of immune status). Antibody detection, made by the Copalis® Immunoassay System, is reported qualitatively for the IgM analytes and semi-quantitatively for the total analyte.

Figure 2:
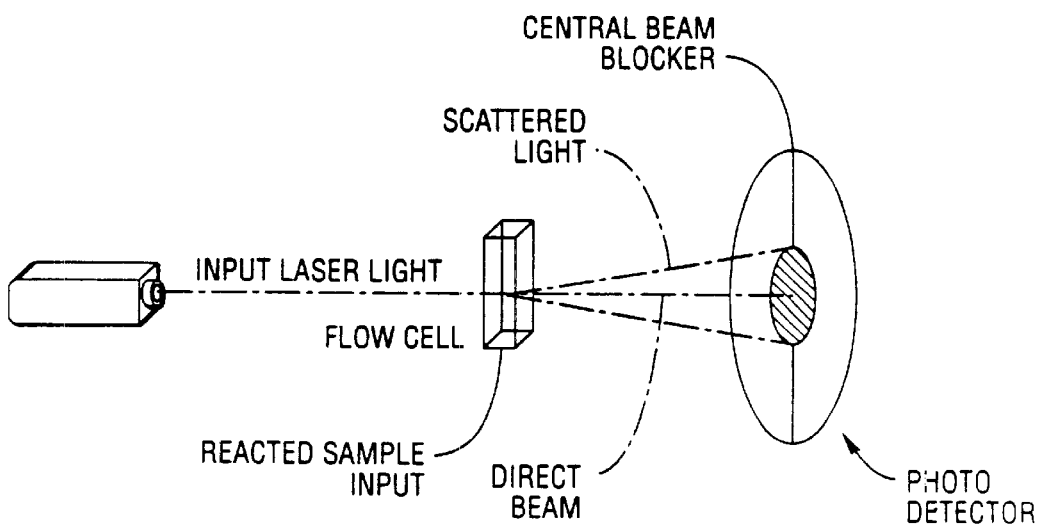
FIG. 2 is an illustration of the Copalis® light scattering analytical equipment.

Copalis® (Coupled Particle Light Scattering) technology is based on the use of high-resolution light scattering analysis to measure particle coupling. As generally depicted in FIG. 2, particles flowing singly through a finely focused optical beam generate a unique light scatter pattern. This scatter pattern is classified into a Copalis® histogram for data analysis.

The Copalis® CMVplex Antibody Assay is based on the principle of antibody dependent particle aggregation as measured by the amount of light scattered. A typical antibody reactivity pattern (IgM and/or IgG) in the patient sample allows diagnosis of the infection as seronegative, acute or past infections. The CMVplex Test Cup has polystyrene microparticles of three sizes each coated with different specific antigens dried in the bottom. The Test Cup is reconstituted with reaction buffer by the instrument. The sample is then transferred into the reaction well and the mixture is agitated for 10 minutes. Upon completion of the agitation, the reaction mixture is transferred to the optical system for analysis.

The level of aggregation is determined by discrimination of particle sizes and unreacted particles (monomers) as detected by the optical system. The quantity of assay particles remaining as monomers is compared to that of an unreacted baseline negative calibrator. A ratio is established between the counts of the two monomer particles. This ratio is reported as the Copalis® Test Result (CTR). The CTR is then converted into a numerical unit, Copalis® Index (CI), which determines the cutoff thresholds for each marker. Interpretation of results is based upon the CI. Results for the IgG marker (VP) are reported semi-quantitatively and qualitatively for the IgM markers (p52 and $CM_2$).

Copalis® CMVplex Antibody Assay—Sized polystyrene microparticles are coated with the following antigens:

1.6µ Viral Particle (VP) obtained from HCMV infected fibroblast cell culture detects long-lasting IgG reactivity 1.7µ recombinant p52 protein full UL44 protein sequence detects IgM reactivity to early phase of acute infection 1.8µ $CM_2$ recombinant protein chimeric antigen containing part of UL44 and part of UL57 detects IgM to both the early and convalescent phases of the acute infection The Copalis® light scattering technique thus allows for detection and precise measurement of antibodies to HCMV. It should be noted that p52 and $CM_2$ antibody may also be detected by ELISA methods.

The EA antibody is measured in the diagnosis of the chronic fatigue syndrome due to Epstein-Barr virus infection. This polymeric EA antibody to diffuse early antigen products is an antibody to as many as 12 nonstructural gene products, which are transactivators for the lytic cycle of Epstein-Barr virus so that the paradigm of complete and incomplete viral multiplication in antibodies in structural and nonstructural epitopes outlined for human cytomegalovirus relates to human Epstein-Barr virus as well. Both, of course, are members of the herpes virus family. The exact number and role of these EBV early proteins remains unclear. These early proteins are involved in transactivation and initiation of the lytic cycle. There are diffuse (EA-D) and (EA-R) restricted components.

In general, herpes viruses such as EBV and HCMV, are characterized by several key properties: (1) their role as a significant pathogen responsible for a variety of diseases; (2) the ability of the herpes virus to remain latent in their host for life, and to be reactivated at or near the site of initial infection; and (3) to multiply efficiently and irreversibly destroy the cells that they infect.

While it is known that antiviral agents are effective in the treatment of viral infections, there are a number of problems associated with such antiviral agents. As the herpes viruses are intracellular parasites which use multiple biochemical pathways of the infected host cell, there are problems associated with achieving clinically useful antiviral activity without also adversely affecting normal host cell metabolism and causing toxicity.

As a selective inhibitor of herpes virus multiplication, acyclovir represents an important advance in antiviral therapy. Acyclovir was synthesized in 1974 by Beauchamp and Schaeffer of Burroughs Wellcome Company. Acyclovir, 9-((2-hydroxyethoxy) methyl) guanine E, demonstrated significant in vitro antiviral activity against herpes viruses, specifically, HSV, varicella zoster virus (VZV) and EBV.

Acyclovir is an acyclic analogue of guanosine. The inhibitory activity of acyclovir is highly selective. The enzyme thymidine kinase (TK) of normal uninfected cells does not effectively use acyclovir as a substrate. However, TK encoded by the herpes simplex virus converts acyclovir into acyclovir monophosphate, a nucleotide analogue. The monophosphate is further converted into diphosphate by cellular guanylate kinase and into triphosphate by a number of cellular enzymes. Acyclovir triphosphate interferes with herpes simplex virus DNA polymerase and inhibits viral DNA replication. Acyclovir is preferentially taken up and selectively converted to the active triphosphate form by herpes virus-infected cells. Acyclovir triphosphate binds viral DNA polymerase, acting as a DNA chain terminator. Because acyclovir is taken up selectively by virus-infected cells, the concentration of acyclovir triphosphate is 40 to 100 times higher in infected cells than in uninfected cells. Furthermore, viral DNA polymerase exhibits a 10 to 30-fold greater affinity for acyclovir triphosphate than do cellular DNA polymerases. The higher concentration of the active triphosphate metabolite in infected cells plus the affinity for viral polymerases results in the very low toxicity of acyclovir for normal host cells.

Acyclovir is available in ointment, capsule and intravenous formulations. Oral acyclovirs or other similar anti-viral drugs are indicated in the management of most cases of primary or initial genital herpes in all patient populations and as long-term suppressive therapy in normal adults with frequently recurrent genital herpes. Oral acyclovir also is used for prophylaxis and treatment of immunocompromised patients with a history of clinical evidence of an active HSV infection. Intravenous acyclovir is used in the treatment of severe primary or initial herpes genitalis of immunocompetent patients, some initial and recurrent mucocutaneous HSV infections in immunocompromised patients, neonatal HSV infections and HSVE in infants, children and adults.

Although EBV and HCMV do not have virus-specific TKs, replication of the EBV and HCMV DNA is significantly impaired. Acyclovir's in vitro antiviral activity is considerably greater in HSV than HCMV.

In addition, acyclovir has an excellent safety profile and is well-tolerated by most patients. The major adverse effect of acyclovir is alteration of renal function. Adequate hydration of patients can prevent renal concretion of drug as it is eliminated by the kidney preventing renal dysfunction.

More recently, Burroughs Wellcome has introduced Valtrex® (valacyclovir hydrochloride) the hydrochloride salt of L-valyl ester of acyclovir. Valacyclovir hydrochloride is L-valine, 2-[(2-amino-1,6-dihydro-6-oxo-9H-purin-9-yl) methoxy]ethylester, monochloride. Valacyclovir has the molecular formula $C_{13}H_{20}N_6O_4,HCl$, a molecular weight of 360.80 and the following structural formula:

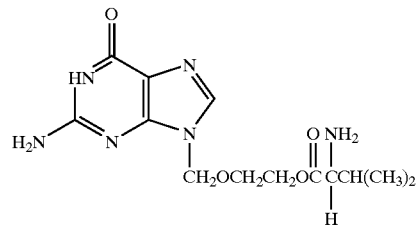

Valacyclovir hydrochloride has a maximum solubility in water at 25° C. of 174 mg/ml.

After oral administration, valacyclovir is rapidly absorbed from the gastrointestinal tract. Valacyclovir is nearly completely converted to acyclovir and an L-valine by first-path intestinal and/or hepatic metabolism. Valacyclovir is rapidly converted to acyclovir, which has in vitro and in vivo inhibitory activity, against herpes simplex virus Types 1 (HSV-1) and 2 (HSV-2) and varicella-zoster virus (VZV). Of these three herpes viruses, acyclovir has highest antiviral effectiveness against herpes simplex virus type 1. The inhibitory activity of acyclovir is highly selective to its affinity for the enzyme thymidine kinase (TK) and encoded by HSV, VZV and Epstein-Barr virus. Thymidine kinase converts acyclovir into acyclovir monophosphate, a nucleotide analog. The monophosphate is further converted into diphosphate by cellular guanylate kinase and into triphosphates, a finite number of cellular enzymes. In vitro, acyclovir triphosphate stops replication of herpes viral DNA. This is accomplished in three ways: (1) competitive inhibition of viral DNA polymerase; (2) incorporation and termination of the growing viral DNA chain; and (3) inactivation of the viral DNA polymerase. The greater antiviral activity of acyclovir against HSV compared to VZV is due to its more efficient phosphorylation by the viral thymidine kinase (TKN). The bioavailability of acyclovir after administration of valacyclovir is 54.5%±9.1% as determined following a one gram oral dose of valacyclovir and a 350 milligram intravenous acyclovir dose.

Valacyclovir is the preferred antiviral agent due to its relatively high bioavailability. As a result of valacyclovir's increased absorption, as compared to acyclovir for example, less frequent dosages of valacyclovir are required to reach effective antiherpetic levels.

Another antiviral agent, ganciclovir, or 9-(1,3-dihydroxy-2-propoxymethyl) guanine, has increased in vitro activity against all herpes viruses as compared to acyclovir, including an 8 to 20 times greater activity against HCMV. While toxicity concerns prevent the use of ganciclovir for a relatively benign HCMV, in other HCMV cases, ganciclovir has become an important antiviral treatment option. While the mode of action of ganciclovir against HCMV and EBV is not entirely known, it has been suggested that these viruses may induce a kinase that efficiently promotes the obligatory initial phosphorylation of ganciclovir to its monophosphate derivative.

Recently, a valine ester prodrug—valganciclovir—was developed to improve the bioavailability of ganciclovir. As compared to ganciclovir, valganciclovir, the 1-valyl ester of ganciclovir, was rapidly and extensively hydrolyzed to ganciclovir, resulting in significantly greater bioavailability compared to 1000 mg oral ganciclovir (60.9% vs. 5.6%, respectively). With significantly greater oral absorption, valganciclovir is believed to be at least as effective as intravenous ganciclovir and thus—preferred for the treatment of HCMV related chronic fatigue syndrome—valganciclovir provides an alternative to intravenous ganciclovir, and eliminates the risk and inconvenience of long term, daily intravenous administration.

Another effective antiviral agent is Vistide®, or cidofovir, 1-[(s)-3-hydroxy-2-(phosphonomethoxy)propyl]cytosine dihydrate with the molecular formula of $C_8H_{14}N_3O_6P.2H_2O$ and a molecular weight of 315.22. Cidofovir again suppresses replication of the herpes virus by selective inhibition of viral DNA synthesis. Cidofovir is incorporated into the growing viral DNA chain which results in reductions in the rate of viral DNA synthesis.

Famvir™, famciclovir is also believed to have antiviral activity against herpes virus 1. Famciclovir is 2-[2-(2-amino-9H-purin-9-yl)ethyl]-1,3-propanediol diacetate. With a molecular formula of $C_{14}H_{19}N_5O_4$ and a molecular weight of 321.3. Famciclovir undergoes rapid biotransformation to the active antiviral compound penciclovir, which has inhibitory activity against herpes simplex virus types 1 and 2 and varicella zoster virus (VZV).

Famciclovir is the diacetyl 6-deoxy analog of the active antiviral compound penciclovir. The absolute bioavailability of famciclovir is 77±8%, as determined from the administration of a 500 mg famciclovir oral dose and a 400 mg penciclovir intravenous dose. In herpes simplex virus 1 and herpes simplex virus 2, viral thymidine kinase phosphorylates penciclovir to its monophosphate form which, in turn, is converted to penciclovir triphosphate by cellular kinases.

In addition, several additional compounds have demonstrated activity against the herpes viruses, antiviral agents which are currently undergoing clinical trial evaluation. Foscarnet sodium (trisodium phosphonoformate) a pyrophosphate analog of phosphono-acetic acid, has potent in vitro and in vivo activity against herpes viruses. Foscarnet inhibits the DNA polymerase of all human herpes viruses by blocking the pyrophosphate binding site which thus prevents chain elongation. A second newly developed antiviral agent is bromovinyl arabinosyl uracil which has exhibited significant inhibition of the herpes simplex virus Type 1, Epstein-Barr virus and the VZV. Fluroiodoarabinosyl cytosine and its related compounds offer another potent inhibitor of herpes viruses. Like acyclovir, this antiviral agent and its activity depends on phosphorylation by herpes virus TK. However, this antiviral agent and its analogs are understood to have greater activity than acyclovir and significant activity against VZV and HCMV. Additionally, (S)-1-((3-hydroxy-2-phosphonyl methoxy)propyl)adenine (HPMPA) is yet another antiviral agent which includes a new class of nucleotide analogs with in vitro activity against HSV 1 and 2, HCMV, VZV and EBV.

Valacyclovir is the preferred antiviral agent for CFS treatment where the etiologic agent is isolated to EBV, due to its relatively high bioavailability. As a result of valacyclovir's increased absorption, as compared to acyclovir for example, less frequent, smaller total dosages of valacyclovir are required to reach effective anti-herpetic levels. Similarly, for CFS treatment, where the etiologic agent is isolated to HCMV, ganciclovir is the preferred antiviral agent. As a result of its increased inhibition of HCMV, ganciclovir is the preferred treatment agent.

The antiviral agent can be administered by any method appropriate, including oral, rectal, nasal, topical, vaginal and parenteral, including subcutaneous, intramuscular, intravenous, intradermal, intrathecal, and epidural. The preferred method is oral.

The amount of antiviral agent required to constitute a "therapeutically effective" amount will vary based on a number of factors including the severity of the chronic fatigue syndrome and the identity and chemical make-up of the patient.

In general, to provide a therapeutically effective amount of the antiviral agent, a suitable effective dose will be in the range of 0.1 to 20 grams per day and preferably in the range between 0.3 and 15 grams per day. An optimum dose is about 0.5 to 10 grams per day. The dosage, of course, varies with the body weight of the patient and so for a 70 kg individual, a dose of 4 grams per day is optimum (e.g., 10 mg. per kg. valacyclovir every 6 hours). In view of toxicity considerations, a maximum for a 70 kg individual is 8–12 grams per day. The desired dose is preferable presented as 2, 3, 4 or more smaller doses administered at appropriate intervals throughout the day. These smaller doses may be administered in unit dosage forms.

In particular for valacyclovir, a patient would be administered a dosage in the range of 0.1 to 50 mg/kg body weight of the patient to 50 mg/kg of body weight of valacyclovir, hydrochloride per dosing interval, generally every six hours. The dosing interval is determined by the bioavailability of the antiviral agent and its excretion from the body. In the preferred embodiment, the patient would be administered a dosage in the range of 0.3 to 40 mg/kg of body weight of valacyclovir, hydrochloride orally every six hours. In the most preferred embodiment, a patient would be administered 10 mg/kg of body weight of valacyclovir, hydrochloride every six hours. These dosage ranges were selected to approximate the pharmacokinetics of intravenous acyclovir, at a dosage schedule of 10 mg/kg of body weight every eight hours intravenously.

The treatment period for a CFS patient varies on a case-by-case basis. It is believed that for some, CFS is an ongoing and persistent problem requiring continued treatment. The duration of the therapy depends on the intensity of the CFS as affected by the therapy. One indicator of an improvement in EBV-isolated CFS patients is a decrease in the level of IgM antibodies to the VCA for EBV. Generally, the therapy duration is proportional to the intensity of the CFS manifestation. Accordingly, following administration of an anti-viral agent, supplemental tests are helpful to check for recurrent CFS and to determine the treatment duration.

While valacyclovir and ganciclovir are the preferred antiviral agents, other antiviral agents which demonstrate anti-herpetic action may be used for the treatment of chronic fatigue syndrome as well. Such antiviral agents may also be effectively administered, for example by oral methods, or as larger doses in time delay formulations. Included among this group of antiviral agents are acyclovir, valacyclovir, famciclovir, cidofovir, and other herpetic antiviral agents and pharmaceutically acceptable derivatives of these antiviral agents. Such pharmaceutically acceptable derivatives include salts, hydrolyzable esters and chelates of the antiviral agents and such similar derivatives which have no negative pharmaceutical effect on the patient upon administration and are thus, "pharmaceutically acceptable." A pharmaceutically acceptable salt is preferably an acidic salt derived from an appropriate acid, for example, hydrochloric, sulfuric, phosphoric, maleic, fumaric, citric, tartaric, lactic, acetic or p-toluenesulphonic acid. Particularly preferred are the hydrochloride salts.

Having generally described this invention, a further understanding can be obtained by reference to certain specific examples which are provided herein for purposes of illustration only and are not intended to be limiting unless otherwise specified.

EXAMPLES

The present inventor has analyzed the effectiveness of various antiviral agents as a method of treatment for patients having chronic fatigue syndrome. As a result of these patient trials, it was found that administration of antiviral agents, even in small doses and over a small period of time, contributed to a significant improvement in the clinical symptoms and signs and to the normalization of the disorder. Tests for EBV and HCMV as Etiologic Agents of CFS

Example 1

Serum antibody titers to Epstein-Barr virus (EBV) and cytomegalovirus (HCMV) were assayed in a consecutive case series of 98 patients with the chronic fatigue syndrome (CFS) at a first clinic visit to a single referral center in Birmingham, Mich. from 1987–1994. Twenty-four percent of the CFS patients had evidence of a cardiomyopathy documented by the presence of abnormal left ventricular dynamics at stress/rest (MUGA) tests. Antibodies to Epstein-Barr virus (EBV) immunofluorescent total early antigens (EA-D) and cytomegalovirus (HCMV) IgM and IgG enzyme immunoassays (ELISA) were measured. The prevalence of these antibodies was compared to that in a non-CFS group of control persons from the same area. Approximately 50% of CFS and non-CFS patients had concurrent EBV multiplication when tested by the presence of an elevated EA antibody titer to the (EAD) diffuse complex which neutralizes EBV encoded DNA polymerase. Elevated IgM HCMV antibodies were uncommon (<10%) in all groups. Approximately 40% of the CFS patients and non-CFS controls had no IgG HCMV antibody. These data are consistent with our understanding that CFS is a persistent cardiomyopathic infection caused by EBV or HCMV, or the two herpes viruses, in combination.

In our additional research efforts, 87 patients with the chronic fatigue syndrome (CFS) studied at a single referral center in Birmingham, Mich. exhibited a primary myocardial disease of unknown cause. These patients exhibited abnormal oscillating T-wave flattenings and T-wave inversions at Holter monitoring, abnormal left ventricular dynamics in stress/rest (MUGA) tests in 24.1% of 87 CFS patients undergoing this study, histopathologic evidence of a cardiomyopathy at right ventricular endomyocardial biopsy and a salutary response to ganciclovir in a small preliminary subset of CFS patients with evidence of cytomegalovirus (HCMV) infection, with no concurrent multiplication of Epstein-Barr virus. These findings are consistent with the cardiac disease that is understood to be the basic pathologic mechanism of the fatigue, exercise intolerance, lightheadedness, left chest ache and palpitations of CFS patients.

Serologic Evidence. In an effort to obtain supportive serologic evidence that the human cardiac myocyte harbors EBV, HCMV or both viruses in CFS patients, we assayed EBV serum antibody total Early Antigen (EA) and IgM antibodies to the viral capsid antigen (VCA) and HCMV IgM and IgG serum antibodies.

However, the diagnosis of another important herpes virus infection, namely, herpes simplex virus (HSV) encephalitis was not possible by tests of specific HSV antibodies in serum. Brain biopsy with isolation of HSV, type 1 or type 2 from affected sites was necessary for diagnosis. It is thus believed that this is also the case for the cardiomyopathy of the CFS.

Patients. From Jan. 1, 1987 through Dec. 31, 1994, ninety-eight CFS patients were seen in a single infectious diseases referral center in Birmingham, Mich. CFS patients met diagnostic criteria outlined by the Centers for the Disease Control and Prevention. CFS cases here are a consecutive case series. Each CFS patient demonstrated abnormal oscillating T-wave flattenings and inversions at Holter monitoring. Twenty-four percent of the CFS patients also demonstrated abnormal left ventricular dynamics by radioisotopic gaited blood pool method. Rest/stress myocardial perfusion studies (thallium 201 or TC-99m sestamibi) or, as necessary, cardiac catheterizations excluded ischemic cardiomyopathy in each case. CFS patient's demographic data were similar to other series. The mean age here was 42.3±10.6 years, and 87% were women. The duration of CFS was 12.2±11.3 months. Other diagnoses were hypercholesterolemia (12%), obesity (6%) and hypertensive vascular disease (3%). No patient had diabetes mellitus.

Antibody Titers. At the initial clinical visit of each CFS patient, EBV total early antigens (EA) immunofluorescent antibody titers (Roche Laboratories, Columbus, Ohio) and cytomegalovirus (HCMV) IgM enzyme immunoassays (ELISA) (Detroit Biomedical Laboratories, Detroit, Mich.) and HCMV ELISA IgG titers (Metpath Laboratories, Teteboro, N.J.) were assayed. The ELISA capture assays includes the steps of capturing the IgG and IgM species onto the solid phase by anti-human immunoglobulin followed by the addition of antigen and labeling the antibodies. With regard to IgM assays, this ELISA method reduces the potential interference of rheumatoid factor. During the EBV infectious lytic cycle, antigen is expressed which can be divided into a diffuse (EA-D) complex and a cytoplasmic restricted (EA-R) complex. We assayed the EA-D. The 52/50 $KD_a$ EA-D protein complex neutralizes EBV encoded DNA polymerase activity. EBV EA antibody indicates recent EBV multiplication (e.g. within 90 days). Likewise, HCMV ELISA IgM enzyme immunoassays indicate recent virus multiplication. A positive HCMV ELISA IgG titer does not differentiate concurrent from past HCMV infection. As a control group to the CFS patients, similar serum antibody titers were measured in 20 random well individuals from the same area. They were 60% women with a mean age of 32 years.

Results

The prevalence of EBV EA antibodies were similar in all CFS patients, both those with and those without abnormal left ventricular dynamics. The prevalence of these EBV antibodies were also the same in non-CFS well persons. Approximately one-half of each of the groups, CFS and non-CFS, had concurrent persistent multiplication of EBV as indicated by an EA antibody titer of $\geq 10$. Similarly, IgG HCMV antibodies were present in approximately 60% of each group. However, HCMV, IgM antibodies were uncommon (<10%).

The research revealed: 1) approximately half of the CFS patients studied had "no evidence of EBV multiplication," when first seen and 2) approximately 40% of the CFS patients had "never been infected with HCMV". These data then are consistent with our understanding that CFS is a persistent infection with either EBV "or" HCMV or, EBV, together with HCMV in the same patient. Proof of this hypothesis requires endomyocardial biopsies of CFS patients with tests of the cardiac tissues for EBV and HCMV nucleic acids by polymerase chain reactions or in-situ hybridization.

Antiviral treatment for an appropriately selected patient is an antiviral drug such as valacyclovir for CFS patients with EBV—positive cardiac biopsies, and an antiviral agent such as ganciclovir for CFS patients with HCMV-positive cardiac biopsies. Dual appropriate anti-viral, anti-HCMV plus anti-EBV therapy is indicated in CFS patients with combined EBV-HCMV infections.

Example 2

EBV-Isolated CFS Patients—Test of Antiviral Treatment. Ten CFS patients, in whom singular Epstein-Barr virus persistent infection was demonstrated, were treated and studied over a six month period. EBV active infection was documented by EBV VCA IgM antibodies and/or EBV EA elevated antibody titers. All of these patients had their energy levels reduced by 50% or more and were partially or entirely non-functional, unable to work or maintain a household. These ten patients had no diseases or complicating conditions which could have accounted for their chronic fatigue syndrome symptoms and they had no prior psychiatric diseases.

Each patient's functional status was recorded as a statistically validated energy index (EI). At each out-patient visit, subjective evaluation of the patient's functional status was recorded using this energy index. The energy index records the average subjective vitality of the patient in the immediate 14 days prior to this specific out-patient visit. When minor illnesses such as the common cold complicated a visit, evaluation of the EI for a patient was delayed until the intercurrent problem receded.

Prior to the initiation of the antiviral treatment and following approximately six months of treatment, objective evaluations of the ability to work and the energy index of each of the ten patients was analyzed. Following the treatment, each of the patients were able to fully engage in his/her activity level at work or home.

Pursuant to the energy index, a patient with a 0 energy index (EI) is bedridden. With an energy index of 1 or 2, any activity by the patient leads to overwhelming, incapacitating fatigue. Such patients are generally light-headed, unable to think clearly, and concentration is difficult for any extended period of time (over 60 minutes). Left-sided chest aches, palpitations, sore throats and feverishness are frequent. These patients may be out of bed for intermittent, brief periods of the day.

Patients with an energy index between 3 and 5 can, with great effort, be out of bed for several hours each day doing non-physical activities. Any exertion significantly worsens the fatigue. These patients express variable light-headedness, inability to think clearly or read normally. Left-sided chest aches, palpitations, sore throats and feverishness occur often. Patients within this energy range cannot perform a 40 hour sedentary job or maintain the duties of a homemaker including such activities as cooking and cleaning. In general, CFS patients have an energy index of 5 or less.

Patients with an energy index between 6 and 9 can assume normal activities and maintain a 40 hour work week and, with pacing, maintain a household. Such patients rarely exhibit light-headedness, foggy thinking, chest aches, palpitations, feverishness and sore throats. These patients can do light physical work or exercise in moderation without fatigue.

Patients with an energy index of 10 have normal energy levels, stamina and a sense of well-being. Light-headedness, difficulties in concentrating and reading ability and chest aches, palpitations, sore throats and feverishness are absent.

This energy index and its validity were tested by the method of construct validity. (Ref. Isaacs and Michael W. B. *Handbook and Research Evaluation*, page 119 Instrumentation and Measurement. Edis E. San Diego, Calif., publishers). In an effort to test the validity of the energy index a random sample of 22 non-CFS persons was compared to 20 CFS patients. The non-CFS persons were 17 women and 5 men with a mean age of 35 years, a median age of 38 years and an overall range between 19 and 62 years. The mean energy index of the non-CFS patients was 9.9, with a median energy index of 10. The CFS patients were 17 women and 3 men with a mean age of 41, median age of 42 and an overall range in years between 16 and 53. The mean energy index of the CFS group was 3.6, with a median of 4. Under Fischer's exact test and T-tests, the gender and ages of the CFS and non-CFS groups were similar. The energy indices of the two groups were markedly different. The power of this T-test is 1. The effect size of these data is 0.25. In comparison, a small effect size is 0.2. A medium effect size is 0.5 and a large effect size is 0.8. Under this scale, the energy index evaluation is a validated term, with a small effect size.

During the initial and final clinical visits, each CFS patient was studied to determine the IgM antibodies to the EBV viral capsid antigen (VCA), total early antigens (EA), and enzyme immunoassays (ELISA) to HCMV IgM and HCMV ELISA IgG titers. An IgM EBV VCA antibody titer indicates infectious lytic EBV multiplication within the most recent 3 month period. During the EBV infectious lytic cycle, antigen is expressed which can be divided into a diffuse (EAD) complex and a cytoplasmic restricted EAR complex (EAR). As a result, each patient's EAD was assayed. The presence of EBV EA antibody indicates current EBV multiplication. Likewise, an elevated cytomegalovirus or Epstein-Barr virus IgM antibody indicates recent EBV or HCMV multiplication, respectively. The EBV VCA antibody IgM titers were done by the ELISA method. As a control group, similar serum antibody titers were measured in 20 non-CFS individuals. In the non-CFS control group, the mean HCMV IgG titer was 240.

Dosage. Each of the patients was administered an oral dose of valacyclovir at 10 mg/kg by mouth every six hours.

Demographics. There were nine women and one man. Their ages ranged from 20–67 years. Their mean age was 43.3 years. None of these ten CFS patients had coronary artery disease as proven by either cardiac catheterization or $T_c99$ sestamibi cardiac stress testing. Two of the ten patients had abnormal left ventricular dynamics by stress MUGA testing. All ten patients had abnormal oscillating T-wave flattenings or T-wave inversions as detected through Holter monitoring studies.

Results

EI Pre and Post Therapy. The mean EI for the 10 patients with EBV CFS was 4.7 and the EI range was 3.5 to 5.5. At the completion of therapy, the same EBV CFS patients had a mean EI 7.5, a median EI of 7, and a range between 6–10. Prior to therapy five out of ten patients had chest pain. At the completion of the trial one out of ten patients had chest pain. At the beginning of the trial, 9 out of 10 patients had light-headedness, unsteadiness, inability to think well. At the completion of the trial, one of ten patients continued to have these symptoms. At the beginning of the trial, five out of ten patients had palpitations, while at the completion of the trial three out of ten patients had palpitations.

Serologic Evidence. Serologic studies of the Epstein-Barr virus VCA IgM titers were done on all patients before the beginning of the trial. They were positive VCA, IgM titers in five out of ten. The remainder of the EBV suspected CFS patients had elevated EBV EA antibody titers. At the completion of the trial, two out of ten continued to have VCA IgM positive titers. At the beginning of the trial, seven out of ten had positive EA antibody titers ($\geq 10$). At the completion of the trial, eight out of ten continued to have positive EA antibody titers. This population of ten patients was characterized by little to no HCMV experience. None had a HCMV IgM titer; eight out of ten had negative CMV IgG titers indicating no experience with this virus. One patient had a titer CMV IgG which was less than 200 and one had a titer greater than 200.

While the foregoing treatments involved administration of valacyclovir or ganciclovir, the test results and the results of treatment are entirely consistent with the postulate that chronic fatigue syndrome is caused by a persistent herpes virus infection, and therefore, treatment by other antiviral agents which demonstrate anti-herpetic antiviral activity may be used for treatment of chronic fatigue syndrome as well. Included among this group of antiviral agents are acyclovir, ganciclovir, valacyclovir, farnciclovir, cidofovir, pharmaceutically accepted derivatives and mixtures thereof and other herpetic antiviral agents used in concentrations which achieve adequate antiviral levels.

Example 3

HCMV-Isolated CFS Patients—Test of Antiviral Treatment. A study was conducted to assess the possible efficacy of ganciclovir treatment on a subset of CFS patients with (1) high HCMV IgG ELISA antibody titers; (2) minimal/no serologic evidence of concurrent EBV multiplication; and (3) oscillating ECG abnormalities at Holter monitoring.

Patients. From March, 1993, through June, 1994, 3 men and 15 women with the mean age of 39.7 plus or minus 7.7 years, with CFS (as defined by the USA, Centers for Diseases Control criteria), were recruited from a single infectious diseases referral center in Birmingham, Mich. Approximately 50 patients with chronic fatigue syndrome were screened for inclusion in this study. The 18 CFS patients studied had a duration of overwhelming fatigue of more than 2 years and with oscillating or repetitively abnormal aberrant T-waves at 24-hour ECG recordings using Holter monitoring. In these 18 CFS patients, baseline standard 12 lead ECG, 2-D echocardiogram, rest-stress myocardial perfusion (thallium 201 or Tc-99 cardiolite) and rest-stress multiple gaited acquisitions (MUGA) studies as well as coronary angiography excluded coronary artery disease. HCMV ELISA and HCMV ELISA IgG titers, as well as EBV capsid antigen (VCA), ELISA IgM and EBV total early antigens (EA) immunofluorescent antibody titers were assayed. Additionally, buffy coats, urine and myocardial biopsies were tested for infectious HCMV. As a control of the occurrence of HCMV and EBV virus antibodies in normal non-CFS persons, residing in the same area, 20 random individuals were tested for HCMV antibodies and for EBV antibodies. Holter monitoring, MUGA studies and endomyocardial biopsies in these patients were done.

Holter monitors, MUGA studies and endomyocardial biopsies were read blindly without knowledge of the patient. Also readings were repeated by at least one, and often several, other physician readers. A patient's 24-hour Holter monitor was considered positive if T-waves became intermittently inverted or flat. Labile T-wave abnormalities at Holter monitoring were present in each CFS patient. In addition to the Holter monitoring, at each outpatient visit, a subjective evaluation of the patient's functional status was recorded using the energy index (EI) as previously described.

Infusions of Ganciclovir. After placement of a peripherally inserted central catheter (PICC) or a groshong catheter, ganciclovir was given intravenously in a dose of 5 mg. per kg. at 12-hour intervals for 30 days. Patients were seen once a week by the same physician and complete blood counts, SMA values and urinalysis were conducted. After 30 days, patients were seen at intervals of 4–6 weeks and evaluated at each of these times. They were advised to avoid exercise, fatigue and alcohol and engage in regular sleeping patterns.

Statistical Methods. Eighteen patients, 3 men and 15 women, all with CFS, with a mean age of 39.7 ranging from 29 to 51 years, were evaluated. Statistical significance between patients meeting the criteria for the HCMV subset and other patients with CFS were evaluated using tests of homogeneity of chi-square analysis and the two-tailed Fisher's exact test for bivariate analysis of dichotomous data.

Results. Of the 18 patients with CFS, 13 patients improved. These 13 patients are hereinafter referred to as "Group A". The gender and ages of CFS patients who improved and the 5 CFS patients that did not improve, these 5 patients are hereinafter referred to as "Group B," were similar. Of the 13 CFS patients that improved, the mean age was 37; among the 5 patients that did not improve, the mean age was 41. One patient in each of the two groups smoked, and a single patient in Group A had an elevated cholesterol level.

The mean duration of fatigue prior to therapy was longer, 2.8 years, in Group B patients versus Group A patients, having a mean duration of 1.6 years. Prior to receiving intravenous ganciclovir, patients in both CFS groups experienced marked worsening fatigue with exercise. Prior to therapy, myalgia, lightheadedness and dull non-specific left-sided chest aches not related to activities were noted in both CFS groups. Other than the above symptoms, physical examinations in all the patients were normal. Two patients in Group A had mitral valve prolapse and another patient in Group A had an occasional mild episode of bronchial asthma. Reactive depressions were more common in Group A. Eight patients in Group A and two patients in Group B complained of difficulty in their ability to concentrate.

Cardiac Studies. Twelve-lead ECG's were normal except for single lead T-wave inversions in standard lead III among 7 patients in Group A and 2 patients in Group B.

After treatment with ganciclovir, 3 patients in Group A with previously abnormal myocardial dynamics reverted to normal and in 3 others, results of MUGA tests improved with lesser degrees of tardokinesis, hypokinesis, or left ventricular dilatation. At follow up 6 months after intravenous ganciclovir treatment, one patient in Group B with an initial normal MUGA study, showed septal hypokinesis. Myocardial perfusion rest-stress studies were normal in 13 of the 14 patients in whom the study was conducted. Right ventricular endomyocardial biopsy showed varying degrees of cardiomyopathic changes characterized by myofiber disarray, myofiber dissolution, myofiber-drop out with fibrous replacement and occasioned myofiber-hypertrophy were evident in 7 of the 14 patients.

HCMV and EBV Antibody Titers. Eight of the patients had high HCMV ELISA IgG antibody titers with a mean of 322 u. Two patients had positive IgM HCMV antibody titers. Ten of the 13 patients had little to no evidence of EBV multiplication as tested by an elevated antibody titer to EA.

Changes in Vitality after Intravenous Ganciclovir Treatment. At the start of ganciclovir, the severity of fatigue based on the energy index, in all patients was similar with a mean of 3 for Group A versus a mean of 2 for Group B. Six months later, the energy indices had increased. Mean indices were 7 and 4 for Groups A and B, respectively. Before therapy with ganciclovir, none of the patients were able to work or function normally. After the antiviral treatment, the 13 patients in Group A, but none of the patients in Group B, resumed their normal pre-CFS activity levels. In general, our studies revealed that patients in Group A had greater improvement than patients in Group B.

Toxicities in Intravenous Ganciclovir. In an initial test, a single patient had a transient increase in serum creatinine, but upon recalculation of dose based upon lean body mass in a repeated test, the serum creatinine level reverted to normal. Similarly, there were no adverse events or symptoms attributable to ganciclovir.

Case Study. A 51-year-old millwright who enjoyed excellent health and whose only risk factor for coronary artery disease was cigarette smoking suddenly experienced overwhelming, progressive fatigue forcing him to stop work. As a result of this fatigue, he was essentially bedridden and slight exertion further worsened his fatigue. He suffered from lightheadedness, generalized muscle aches, intermittent sore throat and an inability to think clearly. The physical exam was normal, chest x-ray, HDL cholesterol levels and urinalysis all were normal. At resting 12-lead ECG showed an inverted T-wave in standard lead III, but was otherwise normal. An ELISA IgM antibody titer to HCMV was positive, while Epstein-Barr virus antibody tests were negative. Holter monitoring showed oscillating abnormal flat or inverted T-waves appearing with the onset of sinus tachycardias, and alternating with the reappearance of normal upright T-waves when tachycardias resolved.

A myocardial sestamibi perfusion rest/stress test showed reversible ischemia of the anterior, apical and inferior walls, but at cardiac catheterization, the coronary arteries were patent. A stress MUGA study revealed abnormal left ventricular function with a resting ejection fraction of 40% (normal >50%).

This patient was given daily intravenous ganciclovir treatments at 5 mg. per kg. every 12 hours, for 30 days. Five months later, the stress MUGA test was repeated and, at this time, the resting ejection fraction had increased 14%, from 40% to 54%, a normal level. Five months later, the patient's maximal cardiac ejection fraction increased from 54% to 68%. At this time, repeat myocardial perfusion studies during exercise were normal. Left ventricular dysfunction was no longer present and the patient's fatigue had disappeared. Subsequently, the patient resumed work as a millwright and after a 2½ year follow-up, remains well with normal left ventricular function.

Conclusion. Based upon these research results, it is understood that CFS patients with a significant ELISA IgG HCMV antibody titer, greater than 120 units, with or without the presence of an IgM HCMV ELISA antibody titer plus an absence of EBV VCA IgM antibody titer along with an EBV EA antibody titer less than 40 describes a group of CFS patients that are understood to derive benefit from ganciclovir treatment. Our research showed a significant and persistent improvement in the patient's energy levels as measured by the energy index. The use of a single thirty-day course of intravenous ganciclovir is arbitrary. Likewise while the above treatments involved ganciclovir, any of the other antiviral agents mentioned herein may be suitable. Further suppressive antiviral therapy with drugs such as an oral preparation of ganciclovir (e.g., cytovene) or oral valacyclovir for EBV CFS patients may be necessary to maintain clinical improvement.

Example 4

HCMV Patients. Results of Copalis® Assays Specificity: The serum of 17 patients were studied who had no cytomegalovirus IgG or IgM antibody to structural viral proteins as measured by the classical ELISA method. In these 17 patients there were no antibodies by the Copalis® method using light scattering technique to either viral protein (VP), $CM_2$ or p52. Therefore, no false-positives by the Copalis® method were seen.

The serum from the 121 separate patients were similarly tested. These patients were positive by the ELISA classical technique for structural cytomegalovirus IgG antibody. They were negative for cytomegalovirus IgM antibody. All 121 of these patients positive for cytomegalovirus IgG antibody were positive for viral protein (Copalis®). The antigen for the cytomegalovirus ELISA technique is nonpurified, human fiberblast tissue culture suspension of tissue-culture-growncytomegalovirus. In every one of these 121 cases which were positive for cytomegalovirus IgG by both Copalis® and ELISA methods, they were negative by Copalis® method for antibodies to p52 and $CM_2$. None of these patients had the chronic fatigue syndrome. There was one patient who was positive in very low titer to cytomegalovirus IgG by the Copalis® method which was negative for IgG antibody to cytomegalovirus by the ELISA method. These data indicate that Copalis® light scatter antibodies do not occur with nonstructural proteins $CM_2$ or p52 in patients with past cytomegalovirus infection. Seventy-six sera were analyzed which were positive for viral capsid antigen IgM to Epstein-Barr virus and/or EA antibody to Epstein-Barr virus. These cases had no cytomegalovirus ELISA IgM or IgG. The obtained serum in 76 cases was uniformly negative by Copalis® tests to human cytomegalovirus IgG and IgM. The IgM includes both nonstructural antibodies $CM_2$ and p52. Therefore Epstein-Barr virus did not cause false-positive Copalis® results. The tests by the Copalis® method are greater than 99 percent specific; false-negatives are extraordinarily rare.

Results of Copalis® antibody testing in patients with the U.S. CDC-Chronic Fatigue Syndrome and various other patients with severe onset of explained fatigue. Group 1) Eight patients were studied with the chronic fatigue syndrome. They are six women and eight men with ages ranging from 32 through 48. They had IgG antibodies to human cytomegalovirus. They had no IgM antibodies to human cytomegalovirus by the ELISA technique. They would be evaluated as having past infection. These eight patients had high titer positive antibodies to nonstructural gene products p52 and $CM_2$. They were treated with intravenous ganciclovir and followed by oral ganciclovir. These nonstructural antibodies became markedly lower and disappeared. Moreover, the fatigue in these patients was remarkably lessened. The use of the Copalis® antibody titer in these patients depicted incomplete virus multiplication and the reversal of this immune status associated with the improvement of the patient with specific anti-viral therapy. Two other patients, two women, a 27 year old woman and a 48 year old woman had similar evidence of chronic fatigue syndrome and high antibody titers to the nonstructural gene products of human cytomegalovirus p52 and $CM_2$. These patients could not be treated with anti-viral agent, ganciclovir. Nevertheless, their initial diagnosis was secured by the presence of the antibodies to p52 and $CM_2$.

Figure 4:
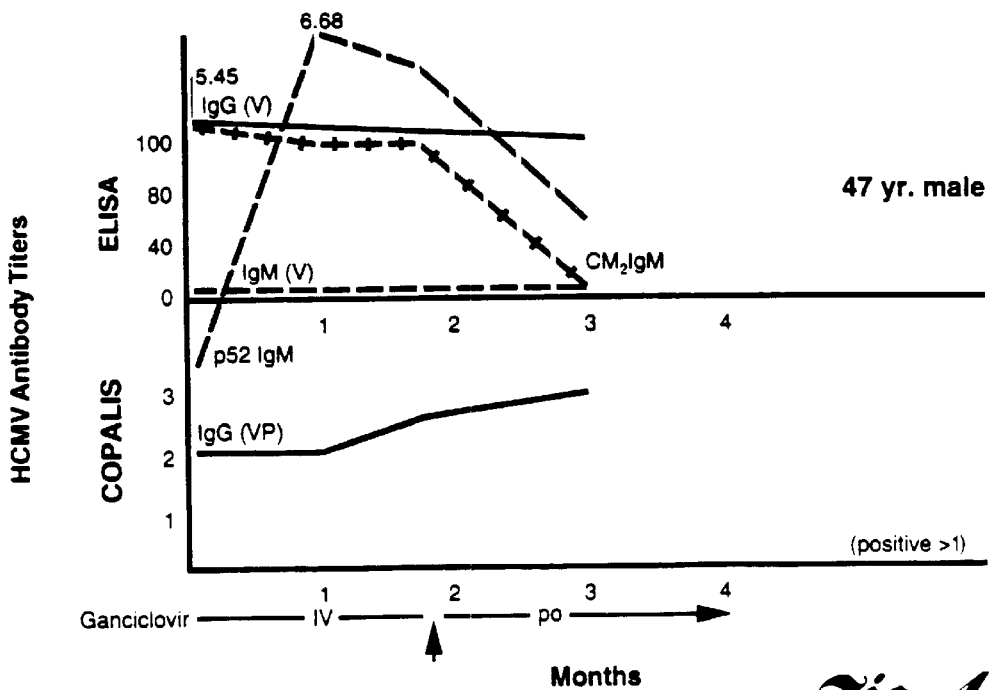
FIG. 4 is a graph depicting a 47-year old male patient's antibody titer levels following the administration of antiviral treatment.

FIG. 4 is a table depicting the antibody titer levels of one of the patients, a 47-year old male, before and after antiviral therapy. This patient had IgG antibodies to HCMV but no IgM antibodies by the ELISA technique. As shown, this patient had high titer positive antibodies to nonstructural gene products p52 and $CM_2$. After antiviral treatment, these nonstructural antibodies became markedly lower.

Three other patients with the chronic fatigue syndrome are of interest. In two of these patients, the patient had, of course, IgG ELISA antibodies to human cytomegalovirus and no IgM antibodies to the ELISA testing. They would be ordinarily read as having past infection. They had, however, markedly high antibody titers to $CM_2$. They had no elevated antibody titers to p52. They were treated with intravenous ganciclovir followed by oral ganciclovir. The $CM_2$ antibodies lessened or disappeared and they improved. The third patient, a 39 year old woman, with chronic fatigue syndrome was diagnosed positive only by the p52 Copalis® method. This patient was similarly treated with intravenous ganciclovir followed by oral ganciclovir and improved remarkably. Therefore, the decreasing response to antibodies to HCMV nonstructural gene products ($CM_2$) after specific antiviral administration defines human cytomegalovirus chronic fatigue syndrome and define three kinds of gene product response. 1) A response to both $CM_2$ and p52; and 2) A response to $CM_2$ only but not p52; 3) A response to p52 but not $CM_2$. Several other patients who had the sudden onset of ongoing, unexplained fatigue also have been studied and found to have antibodies to the p52 and $CM_2$. One of these was an 83 year old woman with congestive heart failure and diabetes mellitus. Her cardiac function improved after intravenous ganciclovir. A second patient is a 75 year old woman with fatigue. Both of these older women had antibody responses to both $CM_2$ and p52. A 60 year old man with morbid obesity and diabetes mellitus suddenly became fatigued with sustained fatigue. He also was identified as having incomplete cytomegalovirus infection by the presence of high titers of the two nonstructural antibodies. Finally, an 82 year old woman had ongoing fatigue of unknown cause. She had antibodies only to the p52 epitopes.

Figure 3:
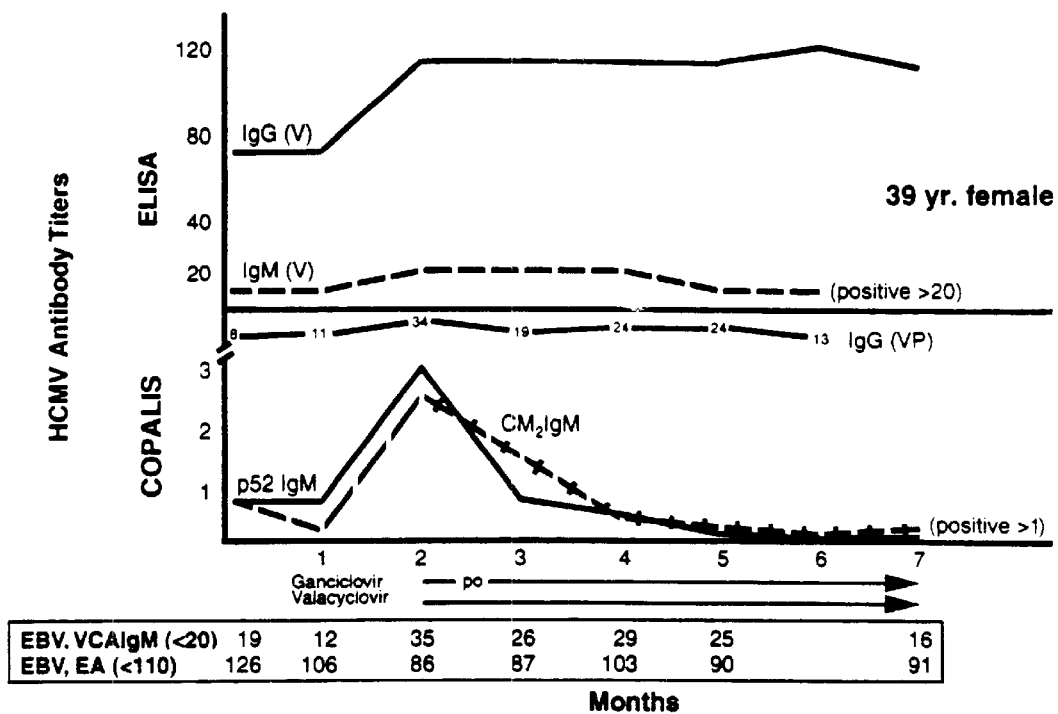
FIG. 3 is a graph depicting a 39-year old female patient's HCMV antibody titer levels following the administration of antiviral treatment.

For illustrative purposes, FIG. 3 depicts a 39-year old female patient diagnosed with variable HCMV-EBV CFS co-infection, having incomplete virus multiplication. As depicted in FIG. 3, the administration of antiviral therapy, specifically both ganciclovir and valacyclovir, remarkably reduced the presence of high antibody titers to both HCMV and EBV.

Conclusion: This invention provides an exact means of diagnosing a subset of patients with cytomegalovirus chronic fatigue syndrome. The decrease in these antibody titers has been identified and the use of specific anti-viral therapy has resulted in significant patient improvement, accompanied by a decrease or disappearance of the fatigue.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of diagnosing and alleviating the symptoms of chronic fatigue syndrome in a patient exhibiting symptoms associated with chronic fatigue syndrome, comprising:
   evaluating the patient for serologic evidence of EBV and HCMV, further comprising:
      obtaining serum from the patient;
      measuring the level of EBV IgM antibodies to the VCA in the serum;
      measuring the level of EBV antibodies to the total EA in the serum;
      measuring the level of HCMV IgM antibodies in the serum by measuring antigens p52 and $CM_2$ with the use of a light scattering technique;
      measuring the level of HCMV IgG antibodies in the serum by measuring antigens p52 and $CM_2$ with the use of a light scattering technique;
   monitoring the patient for T-wave abnormalities;
   classifying EBV as the cause of the chronic fatigue syndrome when the measurements show any one of the following: 1) an elevated level of IgM antibodies to the VCA for EBV; and 2) presence of total EA antibodies for EBV, in combination with the absence of IgM antibodies for HCMV and a low level of IgG antibodies for HCMV;
   classifying HCMV as the cause of the chronic fatigue syndrome when the measurements show any one of the following: 1) an elevated level of IgM antibodies for HCMV; and 2) an elevated level of IgG antibodies for HCMV, in combination with a low level of IgM antibodies to the VCA for EBV, and the absence of total EA antibodies for EBV;

classifying a combination of EBV and HCMV as the cause of the chronic fatigue syndrome when the measurements show any one of the following: 1) an elevated level of IgM antibodies to the VCA for EBV; and 2) the presence of total EA antibodies for EBV, in combination with any of the following: 1) an elevated level of IgM antibodies for HCMV; and 2) an elevated level of IgG antibodies for HCMV;

administering to the patient a therapeutically effective amount of one or more pharmaceutically acceptable antiviral agents suitable for EBV, HCMV or a combination thereof, wherein the one or more antiviral agents are selected from the group consisting of valganciclovir, and pharmaceutically acceptable derivatives and mixtures thereof; and conducting supplemental tests to check for recurrent chronic fatigue syndrome to determine an appropriate treatment period for the patient to achieve continued alleviation of the symptoms of chronic fatigue syndrome.

2. The method of claim 1, wherein the patient is administered 0.1 to 50 milligrams of valganciclovir per kilogram of body weight of the patient over six hours.

* * * * *